(12) United States Patent
Batzinger

(10) Patent No.: US 9,116,098 B2
(45) Date of Patent: Aug. 25, 2015

(54) ULTRASONIC DETECTION METHOD AND SYSTEM

(71) Applicant: GENERAL ELECTRIC COMPANY, Schenectady, NY (US)

(72) Inventor: Thomas James Batzinger, Burnt Hills, NY (US)

( * ) Notice: Subject to any disclaimer, the term of this patent is extended or adjusted under 35 U.S.C. 154(b) by 335 days.

(21) Appl. No.: 13/765,289

(22) Filed: Feb. 12, 2013

(65) Prior Publication Data

US 2014/0224022 A1   Aug. 14, 2014

(51) Int. Cl.
G01N 29/24 (2006.01)
G01N 29/04 (2006.01)
G01N 29/26 (2006.01)
G01N 29/265 (2006.01)

(52) U.S. Cl.
CPC ............ *G01N 29/043* (2013.01); *G01N 29/262* (2013.01); *G01N 29/265* (2013.01); *G01N 2291/0258* (2013.01); *G01N 2291/106* (2013.01); *G01N 2291/2693* (2013.01)

(58) Field of Classification Search
CPC .............. G01N 29/043; G01N 29/265; G01N 2291/0258; G01N 2291/2693; G01N 29/262
USPC .................................. 73/632, 593, 627, 628
See application file for complete search history.

(56) References Cited

U.S. PATENT DOCUMENTS 3,332,278 A   7/1967 Wood et al.
4,497,210 A   2/1985 Uchida et al.
4,523,468 A   6/1985 Derkacs et al.
4,552,021 A   11/1985 Miwa et al.
4,570,487 A   2/1986 Gruber (Continued)

FOREIGN PATENT DOCUMENTS

EP   263475 A3   10/1987
EP   263475 B1   2/1996

(Continued)

OTHER PUBLICATIONS

Moles, Michael. NDT Solution, Construction Weld Testing Procedures Using Ultrasonic Phased Arrays. Copyright 2012, The American Society for Nondestructive Testing. http://www.asnt.org/publications/Materialseval/solution/jan05solution/jan05sol.htm.

(Continued)

*Primary Examiner* — J M Saint Surin
(74) *Attorney, Agent, or Firm* — McNees Wallace & Nurick LLC

(57) ABSTRACT

An ultrasonic detection method and system are disclosed. The ultrasonic detection method includes providing an ultrasonic detection system having a first ultrasonic device arrangement and a second ultrasonic device arrangement, positioning the ultrasonic detection system in a peripheral offset position with respect to an object to be measured, and transmitting and receiving an ultrasonic beam between the first ultrasonic device arrangement and the second ultrasonic device arrangement, thereby obtaining ultrasonic detection information about the object. Additionally or alternatively, the transmitting and receiving of the ultrasonic detection method obtains data on a volume greater than that which is capable of being analyzed by a single probe arrangement. The ultrasonic detection system includes the first ultrasonic device arrangement and the second ultrasonic device arrangement positioned in a peripheral offset position with respect to an object to be measured.

18 Claims, 1 Drawing Sheet

(56) References Cited

U.S. PATENT DOCUMENTS

| | | | |
|---|---|---|---|
| 4,760,737 A | 8/1988 | Kupperman | |
| 4,821,575 A | 4/1989 | Fujikake et al. | |
| 5,445,029 A | 8/1995 | Falsetti | |
| 5,618,994 A | 4/1997 | Falsetti | |
| 5,714,689 A | 2/1998 | Latimer et al. | |
| 5,770,800 A | 6/1998 | Jenkins et al. | |
| 5,963,882 A | 10/1999 | Viertl et al. | |
| 6,019,001 A | 2/2000 | Schreiner et al. | |
| 6,725,722 B1* | 4/2004 | Murphy et al. | 73/628 |
| 7,017,414 B2* | 3/2006 | Falsetti et al. | 73/600 |
| 7,245,789 B2 | 7/2007 | Bates et al. | |
| 7,255,007 B2 | 8/2007 | Messer et al. | |
| 7,302,851 B2 | 12/2007 | Czerw et al. | |
| 7,428,842 B2* | 9/2008 | Fair et al. | 73/626 |
| 7,481,116 B1* | 1/2009 | Osborn | 73/660 |
| 7,654,143 B2* | 2/2010 | Roney et al. | 73/620 |
| 7,775,111 B2* | 8/2010 | Bentzel | 73/627 |
| 7,841,237 B2* | 11/2010 | Suzuki et al. | 73/623 |
| 8,091,424 B2* | 1/2012 | Koinuma | 73/598 |
| 2002/0088282 A1* | 7/2002 | Zayicek et al. | 73/628 |
| 2004/0067000 A1 | 4/2004 | Bates et al. | |
| 2004/0244491 A1 | 12/2004 | Vyas et al. | |
| 2005/0022602 A1 | 2/2005 | Falsetti et al. | |
| 2005/0126291 A1 | 6/2005 | Czerw et al. | |
| 2006/0201252 A1 | 9/2006 | Georgeson et al. | |
| 2007/0000328 A1 | 1/2007 | Buttram | |
| 2007/0119255 A1 | 5/2007 | Czerw et al. | |
| 2007/0157733 A1* | 7/2007 | Litzenberg et al. | 73/644 |
| 2008/0121040 A1 | 5/2008 | MacLauchlan et al. | |
| 2008/0236287 A1* | 10/2008 | Van Agthoven et al. | 73/623 |
| 2009/0095085 A1* | 4/2009 | Koinuma | 73/598 |
| 2009/0320600 A1 | 12/2009 | Koinuma et al. | |
| 2010/0043558 A1 | 2/2010 | Fuller | |
| 2011/0109627 A1 | 5/2011 | Zhang et al. | |
| 2011/0120223 A1 | 5/2011 | McLauchlan et al. | |
| 2011/0277549 A1 | 11/2011 | Frederick et al. | |
| 2011/0296923 A1 | 12/2011 | Cataldo et al. | |
| 2012/0055255 A1 | 3/2012 | Metala et al. | |

FOREIGN PATENT DOCUMENTS

| | | | |
|---|---|---|---|
| EP | 1918701 A1 | | 5/2008 |
| EP | 1927856 A2 | | 6/2008 |
| GB | 2195022 A | | 3/1988 |
| JP | 61080044 A2 | | 4/1986 |
| JP | 5288723 A2 | | 4/1992 |
| JP | 2002310998 A | | 10/2002 |
| JP | 2003337120 | * | 11/2003 |
| JP | 2005315636 A | | 11/2005 |
| JP | 2012042298 | * | 3/2012 |
| WO | 9807373 A1 | | 2/1998 |
| WO | 2009144717 A2 | | 12/2009 |
| WO | 2010097269 A1 | | 9/2010 |
| WO | 2012030520 A1 | | 3/2012 |

OTHER PUBLICATIONS

Granillo, Jesse. Back to Basics, Portable Phased Array Applications. Copyright 2012, The American Society for Nondestructive Testing. http://www.asnt.org/publications/materialseval/basics/apr05basics/apr05basics.htm.

GE Inspection Technologies. Phasor XS—Portable Phased Array Ultrasonic Flaw Dectector. Copyright 2007, General Electric Company. http://www.everestvit.com/download/ultrasound/portable-flaw-detectors/Phasor%20Series/GEIT-20050EN_phasorxs-brochure.pdf.

EP Search Report and Written Opinion issued Jun. 23, 2014 in connection with corresponding EP Patent Application No. 14153940.3.

* cited by examiner

ULTRASONIC DETECTION METHOD AND SYSTEM

FIELD OF THE INVENTION

The present invention is directed to non-destructive testing methods and systems. More specifically, the present invention is directed to ultrasonic detection methods and ultrasonic detection systems.

BACKGROUND OF THE INVENTION

The inspection of large and complex objects (such as, solid steam turbine rotors) can be very difficult. Such inspection is important for identifying features, such as, asperities, voids, defects, fatigued material, cracks, and/or material variations. In large objects, non-destructive techniques are limited based upon the size of the objects, based upon the complexity of the objects, and/or based upon the materials of the objects. A failure to identify such features can result in extended repair cycles, limiting availability of operation, and/or system failure.

Some commercial inspection systems are available to provide the inspection of large objects. Known ultrasonic techniques use single probe approaches, limiting the volume of material that can be inspected in a single pass. For example, one known technique is limited to covering less than 3% of the volume of a cylindrical solid rotor material in a single pass due to geometric features that restrict access to the volume of the rotor.

To achieve such inspection in a non-destructive manner, ultrasonic systems can be integrated into the object at a substantial expense, can require complex and/or repeated analysis, can require advanced motion control and/or complex probe positioning control, and combinations thereof, resulting in high inspection system costs and/or complexity.

An ultrasonic detection method and ultrasonic detection system that do not suffer from one or more of the above drawbacks would be desirable in the art.

BRIEF DESCRIPTION OF THE INVENTION

In an exemplary embodiment, an ultrasonic detection method includes providing an ultrasonic detection system having a first ultrasonic device arrangement and a second ultrasonic device arrangement, positioning the ultrasonic detection system in a peripheral offset position with respect to an object to be measured, and transmitting and receiving an ultrasonic beam between the first ultrasonic device arrangement and the second ultrasonic device arrangement, thereby obtaining ultrasonic detection information about the object.

In another exemplary embodiment, an ultrasonic detection method includes providing an ultrasonic detection system having a first ultrasonic device arrangement and a second ultrasonic device arrangement and transmitting and receiving an ultrasonic beam between the first ultrasonic device arrangement and the second ultrasonic device arrangement. The transmitting and receiving obtains data from a volume greater than that which is capable of being analyzed by a single probe arrangement.

In another exemplary embodiment, an ultrasonic detection system includes a first ultrasonic device arrangement and a second ultrasonic device arrangement positioned in a peripheral offset position with respect to an object to be measured. The ultrasonic detection system is arranged and disposed for transmitting and receiving an ultrasonic beam between the first ultrasonic device arrangement and the second ultrasonic device arrangement, thereby obtaining ultrasonic detection information about the object.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION OF THE INVENTION

Figure 1:
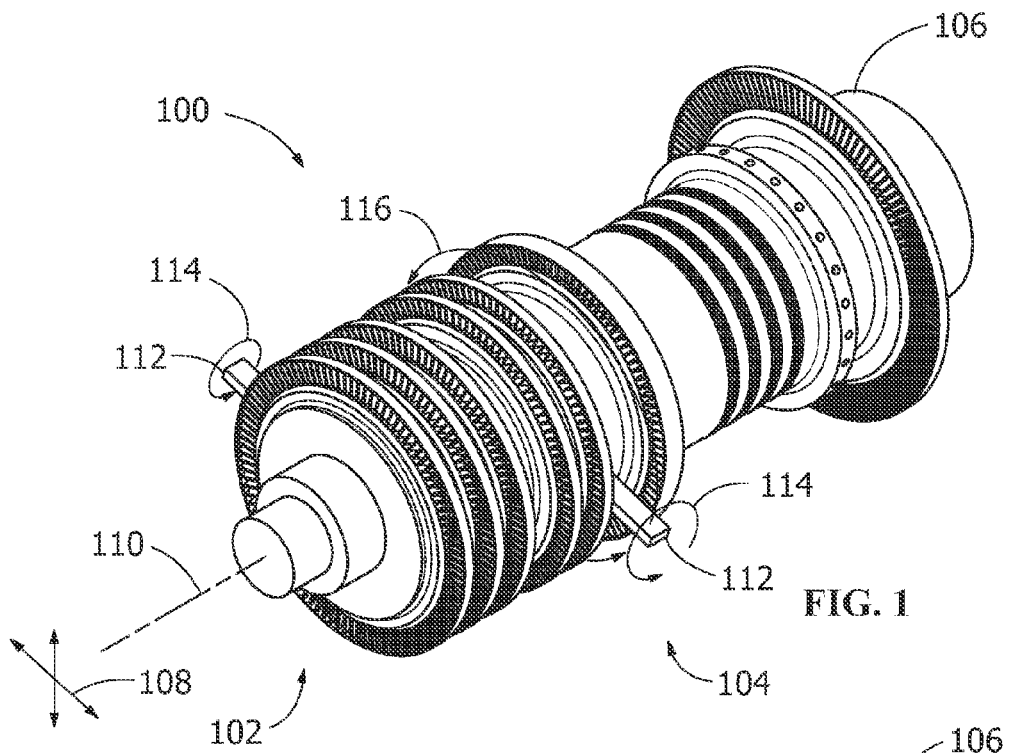
FIG. 1 is a perspective view of an exemplary ultrasonic detection system according to an embodiment of the disclosure.
Figure 2:
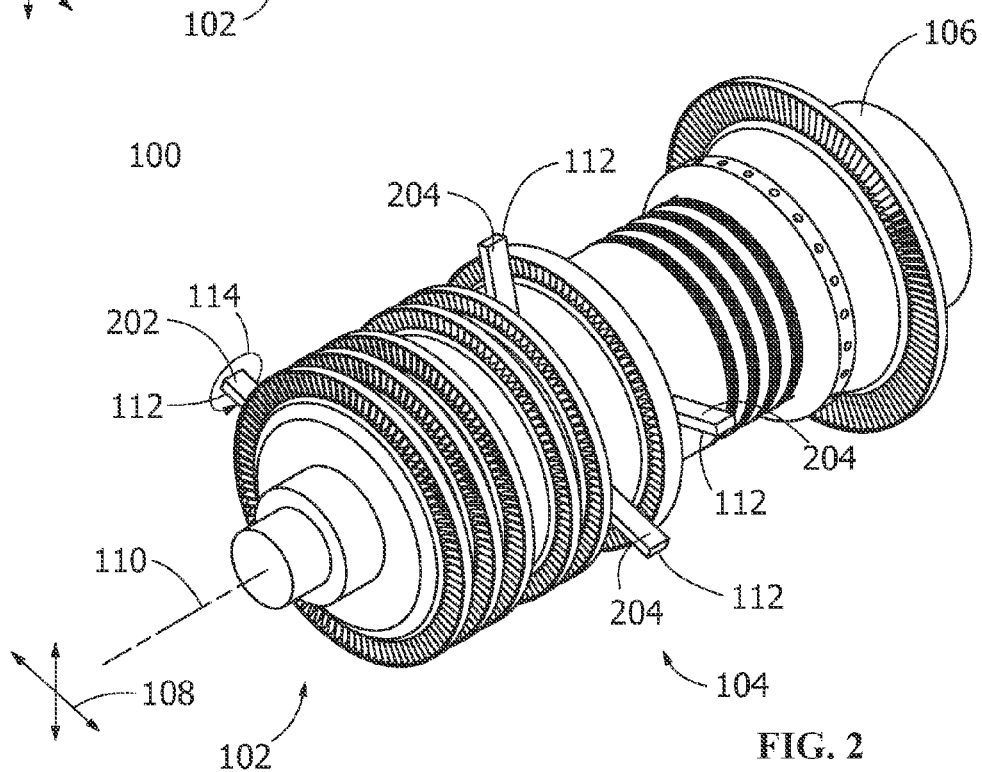
FIG. 2 is a perspective view of an exemplary ultrasonic detection system according to an embodiment of the disclosure.

Provided is an exemplary ultrasonic detection method and system. Embodiments of the present disclosure permit non-destructive analysis of features in large solid or substantially solid objects, reduce or eliminate repair and/or inspection cycles, utilize two or more probes in a pitch-catch manner, analyze a greater volume of cylindrical objects in a single pass, avoid integration of probes into large bodies, reduce or eliminate complex motion control, decrease high costs, permits simplification of data acquisition, permits data analysis of acquired data, or a combination thereof FIGS. 1 and 2 show embodiments of an ultrasonic detection system 100 for performing an ultrasonic detection method. The system 100 includes a first ultrasonic device arrangement 102 and a second ultrasonic device arrangement 104 in a peripheral offset position with respect to an object 106 to be measured. As used herein, the phrase "peripheral offset position" refers to being positioned along an exterior of the object 106 and at a location that is not within a plane 108 extending through the first ultrasonic device arrangement 102 and perpendicularly through a centerline 110 of the object 106.

The system 100 transmits and receives an ultrasonic beam (not shown) between the first ultrasonic device arrangement 102 and the second ultrasonic device arrangement 104, thereby obtaining ultrasonic detection information (not shown) about the object 106. The information detected relates to a volume greater than that which is capable of being analyzed by a single probe arrangement. For example, in embodiments of the present disclosure, an amount of the ultrasonic detection information obtained corresponds to greater than 3% of the volume of the object 106, at least 40% of the volume of the object 106, at least 70% of the volume of the object 106, between about 3% and about 40% of the volume of the object 106, between about 40% and about 60% of the volume of the object 106, between about 70% and about 90% of the volume of the object 106, between about 90% and about 100% of the volume of the object 106, or any suitable combination, sub-combination, range, or sub-range therein. The ultrasonic detection information capable of being obtained includes, but is not limited to, information relating to features selected from the group consisting of voids, defects, fatigued material, cracks, corrosion, and combinations thereof.

The object 106 is any suitable object, such as, a solid body (for example, a metal, metallic, an alloy, a super alloy, etc.), an axially symmetric body (for example, a cylindrical object), a rotor/rotor wheel of a turbine (for example, of a steam turbine), any suitable body of revolution, or a combination thereof. In one embodiment, the object 106 includes geometric features restricting access to portions of the object 106. For example, in an embodiment with the object 106 being a turbine rotor, the wheels restrict access.

In one embodiment, the object 106 has a mass of greater than about 3 Tons, between about 3 Tons and about 40 Tons, between about 20 Tons and about 40 Tons, between about 30 Tons and about 40 Tons, between about 20 Tons and about 30 Tons, about 20 Tons, about 30 Tons, about 40 Tons, or any suitable combination, sub-combination, range, or sub-range therein. In one embodiment with the object 106 being the rotor/rotor wheel, the rotor/rotor wheel is capable of being inspected without a bucket of the turbine being removed.

The first ultrasonic device arrangement 102 and the second ultrasonic device arrangement 104 each include at least one ultrasonic device 112 configured for transmitting (such as a transmitter 202 as shown in FIG. 2) and/or receiving (such as a receiver 204 as shown in FIG. 2) the ultrasonic beam. Each of the ultrasonic devices 112 is a transmitter or receiver, such as, a phased-array ultrasonic having a plurality of ultrasonic transducers (for example, 4 transducers, 8 transducers, 16 transducers, 32 transducers, 64 transducers, or 128 transducers), a predetermined operational frequency (for example, 1 MHz, 1.5 MHz, 2.25 MHz, 3.5 MHz, 5.0 MHz, 7.5 MHz, or 10 MHz), or a combination thereof.

Embodiments of the system 100 include the first ultrasonic device arrangement 102 including a plurality of the ultrasonic devices 112 (for example, two, three, four, or any other suitable number) or having only one of the ultrasonic devices 112. In addition, embodiments of the system 100 include the second ultrasonic device arrangement 104 including a plurality of the ultrasonic devices 112 (for example, two, three, four, or any other suitable number) as is shown in FIG. 2 or having only one of the ultrasonic devices 112 as is shown in FIG. 1.

The system 100 includes the first ultrasonic device arrangement 102 being configured to and/or used for rotational movement, for example, along a rotational path 114 that rotates 360 degrees in a direction parallel or tangential to the centerline 110 of the object. Movement within the rotational path 114 causes the ultrasonic beam to cover a larger volume than a corresponding non-rotating or static use. The movement is at a constant speed, an increasing speed, a decreasing speed, an increasing acceleration, a decreasing acceleration, a constant acceleration, no acceleration, robotically-controlled, or a suitable combination thereof.

As is shown in FIG. 1, in one embodiment, the second ultrasonic device arrangement 104 includes the ultrasonic device 112 being positioned in the peripheral offset position with respect to the ultrasonic device 112 of the first ultrasonic device arrangement 102 and is capable of being or is peripherally adjusted along a peripheral path 116, such as, a circumferential path and/or completely around the object 106, on or proximal to the exterior of the object 106.

As shown in FIG. 2, in one embodiment, the second ultrasonic device arrangement 104 includes a plurality of the ultrasonic devices 112. At least one of the ultrasonic devices 112 is positioned in the peripheral offset position. In one embodiment, a plurality of the ultrasonic devices 112 or all of the ultrasonic devices 112 are positioned in the peripheral offset position. In this embodiment, the system 100 analyzes the object 106 by switching (for example, selectively transmitting and/or receiving) between the ultrasonic devices 112 of the second ultrasonic device arrangement 104 while inspecting and rotating the ultrasonic device(s) 112 of the first ultrasonic device arrangement 102 to align the ultrasonic beam within the object 106. In a further embodiment, the first ultrasonic device arrangement 102 includes the transmitter 202 and the second ultrasonic device arrangement 104 includes a plurality of the receivers 204, specifically shown in FIG. 2 as three of the receivers 204, but, as described above, is any suitable amount.

The transmitter(s) 202, the receiver(s) 204, and/or the ultrasonic device(s) 112 in general are positioned at include angles with respect to each other and/or the object 106 to be measured. In one embodiment, the angles are fixed angles. In one embodiment, the angles of the transmitter (s) 202 and the receiver(s) 204 differ. In one embodiment, the angles of the transmitter (s) 202 and the receiver(s) 204 are the same of substantially the same. Suitable angles include, but are not limited to being arranged, relative to a parallel of the centerline 110, between about 1 degree and about 89 degrees, between about 10 degrees and about 80 degrees, between about 10 degrees and about 60 degrees, between about 45 degrees and about 80 degrees, between about 30 degrees and about 60 degrees, between about 30 degrees and about 45 degrees, between about 45 degrees and about 60 degrees, at about 10 degrees, at about 30 degrees, at about 45 degrees, at about 60 degrees, at about 80 degrees, or any suitable combination, sub-combination, range, or sub-range therein.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An ultrasonic detection method, comprising:
   providing an ultrasonic detection system having a first ultrasonic device arrangement and a second ultrasonic device arrangement;
   positioning the ultrasonic detection system in a peripheral offset position on the exterior of an object to be measured;
   peripherally adjusting at least one ultrasonic device of the second ultrasonic device arrangement along a circumferential path with respect to the object;
   rotating the at least one ultrasonic device of the first ultrasonic device arrangement within a rotation path to form an ultrasonic beam between the first ultrasonic device arrangement and the second ultrasonic device arrangement; and
   transmitting and receiving the ultrasonic beam between the first ultrasonic device arrangement and the second ultrasonic device arrangement, thereby obtaining ultrasonic detection information about the object.

2. The method of claim 1, wherein the second ultrasonic device arrangement includes a plurality of ultrasonic devices.

3. The method of claim 1, wherein the first ultrasonic device arrangement consists of a first ultrasonic device and the second ultrasonic device arrangement consists of a second ultrasonic device.

4. The method of claim 1, wherein the at least one ultrasonic device of the first ultrasonic device arrangement includes a transmitter.

5. The method of claim 1, wherein the at least one ultrasonic device of the first ultrasonic device arrangement includes a receiver.

6. The method of claim 1, wherein the at least one ultrasonic device of the first ultrasonic device arrangement is a phased-array ultrasonic.

7. The method of claim 1, wherein the ultrasonic detection information corresponds to a volume greater than that which would be analyzed by an ultrasonic technique using single probe approaches.

8. The method of claim 1, wherein the ultrasonic detection information corresponds to greater than 3% of the volume of the object.

9. The method of claim 1, wherein the ultrasonic detection information corresponds to at least 47% of the volume of the object.

10. The method of claim 1, wherein the ultrasonic detection information corresponds to about 100% of the volume of the object.

11. The method of claim 1, wherein the object is a solid symmetrical body of rotation.

12. The method of claim 1, wherein the object is a rotor of a turbine.

13. The method of claim 12, wherein the rotor is inspected without a bucket of the turbine being removed.

14. The method of claim 1, wherein the ultrasonic detection information relates to features selected from the group consisting of voids, defects, fatigued material, cracks, corrosion, and combinations thereof.

15. The method of claim 1, further comprising rotating a first ultrasonic device in the first ultrasonic detection device while peripherally adjusting a second ultrasonic device in the second ultrasonic device arrangement with respect to the object, the object being a solid cylindrical body of rotation.

16. The method of claim 1, wherein the second ultrasonic device arrangement includes a plurality of ultrasonic devices and an ultrasonic device of the at least one ultrasonic device of the first ultrasonic device arrangement is rotated within a rotation path to form the ultrasonic beam between the first ultrasonic device arrangement and the second ultrasonic device arrangement.

17. An ultrasonic detection method, comprising:

providing an ultrasonic detection system having a first ultrasonic device arrangement and a second ultrasonic device on the exterior of an object to be measured;

peripherally adjusting at least one ultrasonic device of the second ultrasonic device arrangement along a circumferential path with respect to the object;

rotating the at least one ultrasonic device of the first ultrasonic device arrangement within a rotation path to form an ultrasonic beam between the first ultrasonic device arrangement and the second ultrasonic device arrangement; and transmitting and receiving the ultrasonic beam between the first ultrasonic device arrangement and the second ultrasonic device arrangement;

wherein the transmitting and receiving obtains data a volume greater than that which would be analyzed by an ultrasonic technique using single probe approaches.

18. An ultrasonic detection system, comprising:

a first ultrasonic device arrangement and a second ultrasonic device arrangement positioned in a peripheral offset position on the exterior of an object to be measured, wherein at least one ultrasonic device of the second ultrasonic device arrangement is configured to be peripherally adjusted along a circumferential path with respect to the object;

wherein the at least one ultrasonic device of the first ultrasonic device arrangement is configured to be rotated within a rotation path to form an ultrasonic beam between the first ultrasonic device arrangement and the second ultrasonic device arrangement, and wherein the ultrasonic detection system is arranged and disposed for transmitting and receiving the ultrasonic beam between the first ultrasonic device arrangement and the second ultrasonic device arrangement, thereby obtaining ultrasonic detection information about the object.

* * * * *